(12) United States Patent
Christoffel et al.

(10) Patent No.: US 6,702,798 B2
(45) Date of Patent: Mar. 9, 2004

(54) FOLDED ABSORBENT ARTICLE

(75) Inventors: Paul William Christoffel, Appleton, WI (US); Joel Curtis Krueger, Oshkosh, WI (US); Mark John Jung, Menasha, WI (US); Willard Frances Hawley, Jr., Seymour, WI (US); Steven Charles Schapel, Appleton, WI (US); Mark David Spiegelberg, Neenah, WI (US); Jeffery Michael Tabor, Appleton, WI (US); Mark Joseph VanGroll, Kaukauna, WI (US); Mark James VanRossum, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 253 days.

(21) Appl. No.: 09/931,202

(22) Filed: Aug. 16, 2001

(65) Prior Publication Data

US 2003/0036739 A1 Feb. 20, 2003

(51) Int. Cl.⁷ ................................. A61F 13/15
(52) U.S. Cl. ....................... 604/385.201; 604/385.01
(58) Field of Search ................ 604/385.201, 385.01, 604/396, 394; 493/395–399, 405; 206/440, 494, 499, 526; 53/429, 436

(56) References Cited

U.S. PATENT DOCUMENTS

| | | | |
|---|---|---|---|
| 3,938,523 A | | 2/1976 | Gilliland et al. |
| 3,963,029 A | * | 6/1976 | Brooks ........................ 604/289 |
| 3,978,861 A | * | 9/1976 | Schaar ........................ 128/287 |
| 4,326,528 A | | 4/1982 | Ryan et al. |
| 4,802,884 A | * | 2/1989 | Froidh et al. ................ 493/339 |
| 6,050,984 A | | 4/2000 | Fujioka et al. |
| 6,079,562 A | | 6/2000 | Bauer et al. |
| 6,626,881 B2 | * | 9/2003 | Shingu et al. ........ 604/385.201 |

FOREIGN PATENT DOCUMENTS

| | | |
|---|---|---|
| EP | 0 254 700 A2 | 1/1988 |
| EP | 0 452 951 B1 | 11/1995 |
| EP | 0 947 446 A1 | 10/1999 |
| EP | 0 988 846 A2 | 3/2000 |
| GB | 2 245 149 B | 1/1992 |
| JP | 3021190 U | 2/1996 |
| JP | 3055348 U | 1/1999 |
| JP | 11-113956 A2 | 4/1999 |

OTHER PUBLICATIONS

Patent Abstracts of Japan JP 03–021238 A2: Description of Tabata Kenichi, "Paper Diaper."
Patent Abstracts of Japan JP 2000–024029 A: Description of KAO Corp., "Package Structure of Shorts Type Absorptive Article."
Patent Abstracts of Japan JP 2001–019070 A: Description of KAO Corp., "Individual Packing Structure for Absorbent Article."

* cited by examiner

Primary Examiner—Weilun Lo
Assistant Examiner—Jacqueline F Stephens
(74) Attorney, Agent, or Firm—Thomas J. Connelly

(57) ABSTRACT

A folded absorbent article including a front portion, back portion, and an intermediate crotch portion. The front portion joins the back portion by first and second side seams forming a waist opening and leg openings. Each of the front and back portions includes a demarcation line positioned between first and second zones. Each of the front and back portions includes a first section, a second section, and a third section. The first section is longitudinally folded over the second section providing a first side seam positioned laterally outboard of a longitudinal centerline of the absorbent article to form a first longitudinal fold line. The third section is folded over the first section providing the second side seam positioned laterally outboard of the longitudinal centerline to form a second longitudinal fold line. The first zone is transversely folded along the demarcation line over a portion of the crotch forming a folded absorbent article.

20 Claims, 5 Drawing Sheets

FOLDED ABSORBENT ARTICLE

FIELD OF THE INVENTION

This invention relates to a folded absorbent article. More specifically, this invention relates to a folded absorbent that is compact, easily removed from a plastic package, and can be readily unfolded for application to a human torso.

BACKGROUND OF THE INVENTION

Absorbent articles of the type generally known as training pants or disposable underpants for use by infants, toddlers, and incontinent adults are well known in the art. A variety of such absorbent articles that utilize various folded configurations are commercially available. Many of such articles are folded to create a generally rectangular shape to allow a number of folded articles to be efficiently placed within a single package, to reduce package size, or to maintain the shape of the package. Often the absorbent core of these articles is transversely folded in order to achieve the desired rectangular shape. However, such transverse folds, typically occurring near the longitudinal end margins of the absorbent core, can compromise the effectiveness and function of the article when in use by the consumer. For example, the absorbent and wicking capacities of the absorbent core can be reduced or disrupted where the core is folded due to compression of the fibers or separation of the absorbent core into two or more noncontiguous sections. Furthermore, the end margin of the absorbent core can be deflected away from the plane of the absorbent core resulting in a less comfortable fit and an increased likelihood of urine or fecal leakage. In addition, many of the training pant products contain elastic materials in only a portion of the torso covering part of the product. Because of this positioning of the elastic materials, the products often have an unelasticized portion that can bunch or crimp during the folding process resulting in a bulkier product or a product that is difficult to handle during the packaging process.

Now, a folded absorbent article has been developed that has the desired rectangular shape but is transversely folded in a portion of the absorbent article spaced away from the longitudinal edges of the absorbent core. Folding the absorbent article at a transverse demarcation line positioned away from the longitudinal edges of the absorbent core eliminates transverse folding of the absorbent core and can improve the effectiveness, fit and comfort of the absorbent article in use by the consumer. Furthermore, the desired rectangular shape is retained while the overall bulk of the folded article is reduced allowing for easier packaging. In addition, the absorbent article is longitudinally folded at a line adjacent to the side edges of the absorbent core such that the side seams of the absorbent article extend laterally outboard of the longitudinal centerline of the product. By longitudinally folding the absorbent article in this manner, the unelasticized portions of the article are contained within the folded absorbent article thereby reducing bunching and/or crimping of the unelasticized portions and providing a smaller, neater folded absorbent article that is easier to handle during the packaging process.

SUMMARY OF THE INVENTION

Briefly, this invention relates to a folded absorbent article. The absorbent article includes a front portion and a back portion joined together by a crotch portion. An absorbent core is positioned in the crotch section. The front portion is joined to the back portion of the article by first and second side seams in order to form an absorbent article having a waist opening and a pair of leg openings. Elastic is positioned in the front and/or back portions to define an elastic waistband. Each of the front and back portions includes a first zone and a second zone with a transverse demarcation line positioned therebetween. Each of the front and back portions further includes a first section, a second section and a third section. The first section is longitudinally folded over the second section such that the first side seam is positioned substantially laterally outboard of a longitudinal centerline of the absorbent article to form a first longitudinal fold line. The third section is longitudinally folded over the first section such that the second side seam is positioned substantially laterally outboard of the longitudinal centerline to form a second longitudinal fold line. The first zone is transversely folded along the demarcation line over at least a portion of the crotch portion to form a folded absorbent article.

In another embodiment, the first section of the front and back portions of the absorbent article is longitudinally folded over the second section such that the first side seam is positioned laterally outboard of a longitudinal centerline of the absorbent product to form a first longitudinal fold line. The first section is longitudinally folded to form a third longitudinal fold line such that the first side seam is positioned adjacent to the first longitudinal fold line to form a longitudinal pleat in the first section. The third section is longitudinally folded over the first section such that the second side seam is positioned laterally outboard of the longitudinal centerline to form a second longitudinal fold line. The first zone is transversely folded over along the demarcation line over at least a portion of the crotch portion to form a folded absorbent article.

The general object of this invention is to provide a folded absorbent article. A more specific object of this invention is to provide a folded absorbent article having a first section of the front and back sections of an absorbent article folded longitudinally over a second section of the absorbent article such that the first side seam is positioned laterally outboard of the longitudinal centerline of the absorbent article, a third section longitudinally folded over the first section of the absorbent article such that the second side seam is positioned laterally outboard of the longitudinal centerline of the absorbent article, and a first zone of the front and back portions of the absorbent article transversely folded along a demarcation line positioned between the first zone and a second zone of the front and back portions of the absorbent article over at least a portion of the crotch portion.

Another object of this invention is to provide a folded absorbent article that is generally rectangular in shape.

A further object of this invention is to provide a folded absorbent article that is transversely folded in a portion of the absorbent article that is positioned away from the ends of the absorbent core to reduce disruption of the absorbent core during packing and storing and to improve the effectiveness, fit and comfort of the absorbent article during use by consumer.

Still another object of this invention is to provide a folded absorbent article that has a reduced bulk to allow for more compact packaging.

Still further, an object of this invention is to provide a folded absorbent article that is longitudinally folded such that the unelasticized portions of the front and back portions of the absorbent article are contained within the folded absorbent article to provide a neater folded article that is easier to handle during the packaging process.

Other objects and advantages of the present invention will become more apparent to those skilled in the art in view of the following description and the accompanying drawings.

DETAILED DESCRIPTION OF THE PREFERRED EMBODIMENTS

Figure 1:
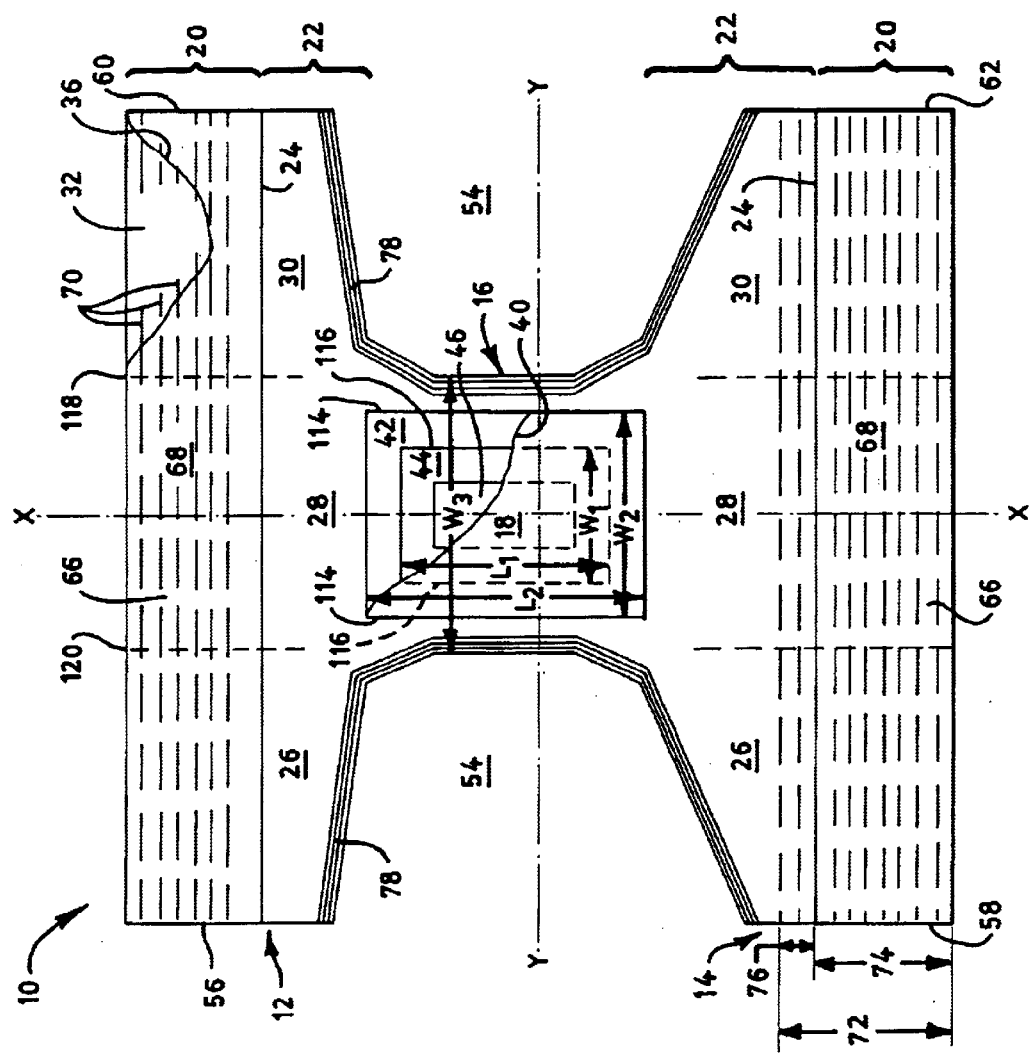
FIG. 1 is a top view of an absorbent article having a back portion, a front portion, and a crotch portion with cut-away views to show underlying elements.
Figure 2:
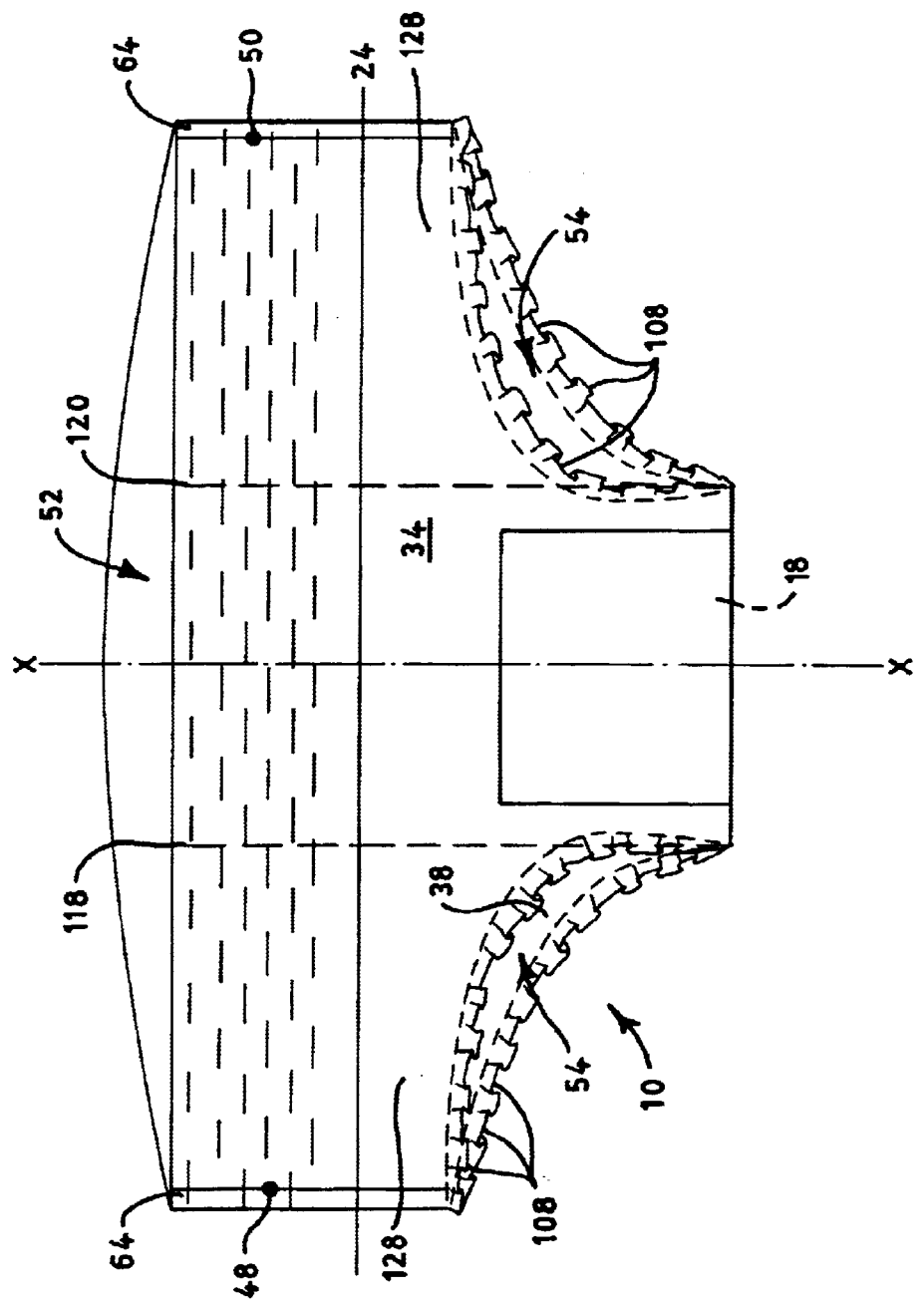
FIG. 2 is a perspective view of the absorbent article when the front and back portions are joined together.

Referring to FIGS. 1 and 2, the absorbent article 10 is shown in a flat configuration prior to being formed into a pant-like absorbent article. The pant-like product is depicted in FIG. 2. The absorbent article 10 has a front portion 12 joined to a back portion 14 by a crotch portion 16. An absorbent core 18 is positioned in the crotch portion 16. The absorbent article 10 has a longitudinal centerline X—X and a transverse centerline Y—Y. Each of the front portion 12 and back portion 14 have a first zone 20 and a second zone 22 with a transverse demarcation line 24 positioned therebetween. The second zone 22 is disposed between the transverse demarcation line 24 and the crotch portion 16. Further, each of the front and back portions, 12 and 14 respectively, have a first section 26, a second section 28, and a third section 30.

Preferably, the front portion 12, the back portion 14 and the crotch portion 16 include an outer cover 32 that forms the exterior surface 34, see FIG. 2, of the absorbent article 10. The outer cover 32 is located away from the body of the wearer in use. The outer cover 32 can be a single piece of material or it can be made up of two or more separate pieces of material that are joined together. The outer cover 32 should be formed from a soft and flexible material and it can be either liquid-permeable or liquid impermeable. Preferably, the outer cover 32 is liquid impermeable. In some instances, it may be advantageous to form the outer cover 32 from a liquid impermeable material that will allow vapor to pass through but which will prevent body fluid from passing through. A suitable material for the outer cover 32 can be made from natural or synthetic fibers and/or films. Examples of natural fibers include cellulose wood fibers and cotton fibers. Examples of synthetic fibers include rayon fibers, polyester fibers and polypropylene fibers. When a film is utilized, a thermoplastic film formed from a polyolefin, such as polypropylene or polyethylene, works well. A combination of natural and synthetic materials can also be used to construct the outer cover 32. The outer cover 32 can be formed from a woven or non-woven web. The outer cover 32 can further be formed from a sheet of spunbond, meltblown or a bonded-carded web or from a laminate formed from any of the above-identified material.

The front portion 12, back portion 14 and the crotch portion 16 also include a bodyside liner 36 that forms the bodyside surface 38, see FIG. 2, of the absorbent article 10. The bodyside liner 36 is located toward the body of the wearer in use. The bodyside liner 36 may be one piece of material or it can be made up of several pieces of material that are joined together. The bodyside liner 36 should be formed from a soft and flexible material and it can be either liquid permeable or liquid impermeable. Preferably the bodyside liner 36 is liquid permeable. The bodyside liner 36 can be formed from a non-woven web, a spunbond, a meltblown, or a bonded carded web composed of synthetic polymer filaments or fibers. Examples of synthetic materials include polypropylene, polyethylene, polyesters and the like.

The bodyside liner 36 can be attached or secured to the outer cover 32 by an adhesive, by sewing, by a pressure bond, by a thermal bond, by a pressure and thermal bond, or by another means known to those skilled in the art. The absorbent core 18 can be disposed between the outer cover 32 and the bodyside liner 36 in the crotch portion 16 of the absorbent article 10. Alternatively, the absorbent core 18 can be positioned in the crotch portion 16 to overlay the bodyside liner 36. The absorbent core 18 may be secured to the crotch portion 16 of the absorbent article by an adhesive or by other means known to those skilled in the art.

Still referring to FIGS. 1 and 2, an absorbent core 18 is shown positioned in the crotch portion 16 of the absorbent article 10 overlaying the bodyside liner 36. The absorbent core 18 includes a liquid permeable cover 40, a liquid impermeable baffle 42 and an absorbent layer 44 positioned therebetween. The liquid permeable cover 40 and the liquid permeable baffle 42 are joined together, preferably about their peripheries. The cover 40 and the baffle 42 may be joined together by an adhesive, by sewing, by a pressure bond, by a thermal bond, by a pressure and thermal bond, or by another means known to those skilled in the art.

The absorbent layer 44 has a length $L_1$ and a width $W_1$ and the absorbent core 18 has a length $L_2$ and a width $W_2$. Preferably, $L_1$ and $W_1$ are less than $L_2$ and $W_2$, see FIG. 1. This means that the liquid permeable cover 40 and the liquid impermeable baffle 42 are larger in size than the absorbent layer 44 and both extend beyond the outer periphery of the absorbent layer 44. This is important because by forming the absorbent layer 44 such that it has a smaller overall size, any body fluid received by the absorbent layer 44 will not be able to flow or wick outward to the outer edges of the absorbent core 18. This feature will minimize and hopefully prevent the chance of fluid leakage from occurring.

The liquid permeable cover 40 can be formed from a liquid permeable material so as to allow body fluid that strikes the absorbent core 18 to pass down into the absorbent layer 44. The liquid permeable cover 40 can be formed from a non-woven web, a spunbond, a meltblown or a bonded-carded web composed of synthetic polymer filaments or fibers. Examples of synthetic materials include polypropylene, polyethylene, polyesters and the like. The liquid permeable cover 40 can also be formed from a perforated thermoplastic film. Other materials, which can also be utilized to form the cover 40, include rayon and cotton. The liquid permeable cover 40 can be treated with a surfactant to aid in transfer of body fluid into the absorbent layer 44, if desired.

The liquid impermeable baffle 42 can be formed from a liquid impermeable material so as to prevent body fluid that contacts it from passing therethrough. The liquid impermeable baffle 42 can be formed from a thin sheet of thermoplastic material such as polyethylene, polypropylene, polyvinyl chloride and the like. Alternatively, the liquid impermeable baffle 42 can be a non-woven, fibrous web that has been constructed to have low liquid permeability. The liquid impermeable baffle 42 can also be constructed from a foam material. In some instances, it may be advantageous to form the liquid impermeable baffle 42 from a material that will allow vapor to pass through but which will prevent body fluid from passing through.

The absorbent layer 44 that is retained between the liquid-permeable cover 40 and the liquid impermeable baffle 42 should be designed to absorb urine. However, it could be constructed to absorb other body fluids such as menses, blood, perspiration, as well as other body excrements. The absorbent layer 44 can be formed from various natural and/or synthetic materials, such as cellulose fibers, wood pulp fibers, regenerated cellulose or cotton fibers, meltblown fibers, a blend of pulp and other fibers, or a combination of various fibers. A suitable material is "coform" which is a mixture of cellulose fibers and synthetic polymer fibers. Coform is manufactured by Kimberly-Clark Corporation having an office at 401 North Lake Street Neenah, Wis., 54956.

The absorbent layer 44 can also include superabsorbent materials, commonly referred to as "superabsorbents", to increase its absorbency and ability to retain body fluids under pressure loads. The superabsorbents can be present in particle form, as fibers, flakes or in some other structural shape. The superabsorbents can be secured to the absorbent fibers by an adhesive or they can be loosely positioned between the absorbent fibers. Suitable superabsorbents are commercially available from Dow Chemical Company, Hoechst Celanese Corporation and Allied Colloids, Inc.

Figure 3:
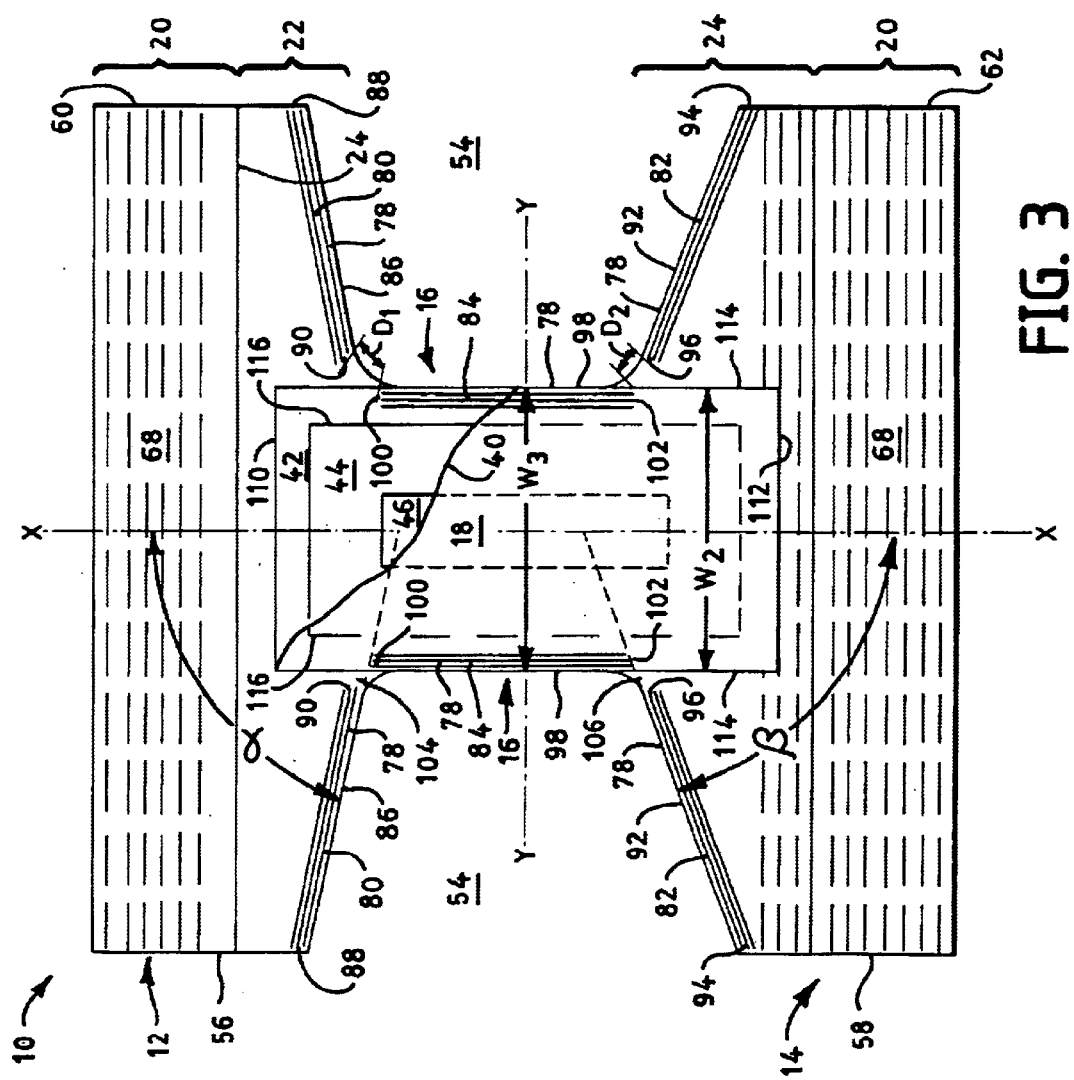
FIG. 3 is a top view of an alternative embodiment showing the absorbent core extending into the second zone of the front and back portions of the absorbent article and leg elastic having front, back and crotch sections separated by a gap.

The absorbent layer 44 can be wrapped in tissue or be associated with some similar kind of acquisition and/or distribution layer to assist in maintaining the integrity of the absorbent fibers and the superabsorbents. In FIGS. 1 and 3, the absorbent layer 44 is depicted as having a rectangular shape but it could be formed into other shapes as well, including an hourglass shape, an oval shape, an I-beam shape, a T-shape or a keyhole shape amongst others.

A surge layer 46, also commonly referred to as an acquisition/distribution layer, can optionally be positioned above the absorbent layer 44. The surge layer 46 can be in direct contact with the liquid permeable cover 40. The purpose of the surge layer 46 is to quickly take up body fluid that contacts the cover 40 and direct this fluid downward toward the absorbent layer 44. In addition, the surge layer 46 can direct the body fluid outward in the transverse and/or longitudinal directions so that the fluid is capable of contacting a greater surface area of the absorbent layer 44. This ability to quickly move the body fluid in the x, and/or y, and z directions diffuses surges of body fluid that insult the absorbent core 18. The surge layer 46 can be formed from a through-air bonded carded web composed of a blend of 40 percent 6 denier polyester fibers, commercially available from Hoescht Celanese Corporation, and 60 percent 3 denier polypropylene/polyethylene sheath/core bicomponent fibers, commercially available from Chisso Corporation. The surge layer 46 can have an overall basis weight ranging from about 50 grams per square meter (gsm) to about 120 gsm. In FIG. 1, the surge layer 46 is depicted as having a rectangular configuration but it could be formed into any other shapes as well, including a hourglass shape, an oval shape, etc.

Referring to FIGS. 1 and 2, the pant-like absorbent article 10 is formed when the front portion 12 is joined to the back portion 14 by a first side seam 48 and a second side seam 50 to form a waist opening 52 and pair of leg openings 54. Returning to FIG. 1, a first front side edge 56 is joined to a first back side edge 58 to form the first side seam 48 and a second front side edge 60 is joined to a second back side edge 62 to form the second side seam 50. The first side edges, 56 and 58 respectively, and the second side edges, 60 and 62 respectively, may be joined by any means known in the art such as, among others, adhesive or heat bonding, ultrasonic welding or a combination of one or more means. It should be noted that any salvage 64 formed by joining seam 48 or 50 should be oriented toward the exterior surface 34 of the absorbent article 10, a shown in FIG. 2, to provide a more comfortable and less irritating fit around the wearer's torso.

Referring again to FIG. 1, elastic 66 is positioned in one or both of the front portion 12 and the back portion 14 to define an elastic waistband 68. The elastic 66 can be attached to the absorbent article 10 sandwiched between the outer cover 32 and the body side liner 36 in generally a stretched state by means known in the art, including ultrasonic bonded, heat/pressure bonded or adhesively bonded. The elastic 66 may be transversely positioned across at least a portion of the first zone 20 of the front portion 12 and/or the back portion 14 to form the elastic waistband 68. The elastic 66 can include threads, strands, ribbons, bands, film elastic non-wovens or composites. The threads, strands, ribbons, etc. may be a multitude of singular members or they may be applied as a composite. The elastic 66 can be applied to the absorbent article 10 under an elongation ranging from between about 100 percent to about 400 percent, more preferably, under an elongation ranging from between about 150 percent to about 300 percent, and, most preferably, under an elongation ranging from between about 200 percent to about 275 percent. The elongation of the elastic 66 in the front portion 12 can be equal to or different than the elongation of the elastic 66 in the back portion 14.

Preferably, the elastic waistband 68 may be comprised of multiple elastic strands 70. The number of elastic strands 70 can range from 1 to over 100. Preferably, the number of elastic strands 70 will range from between about 10 to about 40, and most preferably, from about 15 to about 35. The number of elastic strands 70 in the front portion 12 can be equal in number or be different in number than the number of elastic strands 70 in the back portion 14. The elastic strands 70 may be uniformly spaced apart from each other or non-uniformly spaced apart from each other. Further, at least one of the elastic strands 70 may be positioned in the front portion 12 at least about 0.25 inches (0.64 centimeters) above the demarcation line 24 in the first zone 20. Alternatively, at least one of the elastic strands 70 may abut the demarcation line 24 in the first zone 20 of the front portion 12 of the absorbent article 10. Individual elastic strands can be applied under the same or a different elongation.

The elastic strands 70 may be made from any suitable elastomeric material. One suitable material is LYCRA®.

LYCRA® is a registered trademark of E. I. DuPont de Nemours & Company, a business that has offices at 1002 Market Street, Wilmington, Del., 19801. Suitable elastic strands 70 include strands having a decitex (grams/10,000 meters) ranging from between about 100 to about 1,200, preferably, ranging from between about 470 to about 940, and most preferably, ranging from between about 620 to about 740. The elastic strands 70 can be secured to the outer cover 32 and/or to the bodyside liner 36 by a hot or cold melt adhesive applied in a variety of spray patterns. One spray pattern that has been used with good success is a swirl pattern. A preferred adhesive is a hot melt adhesive sold as Findley H2096 by ATO Findley Adhesives having offices in Milwaukee, Wis.

The elastic strands 70 allow gathers (not shown) to form about the waist opening 52, see FIG. 2, to prevent leakage from the absorbent article 10. The number of gathers formed will depend on the number of elastic strands 70 present, the spacing between each of the strands 70, the contraction force of the elastic strands 70, the material from which the outer cover 32 and the bodyside liner 36 are constructed, as well as other factors.

Still referring to FIG. 1, the elastic waistband 68 can cover a distance 72, measured parallel to longitudinal centerline X—X, of between about 0.5 inches (1.27 cm) to about 10 inches (25.4 cm). The elastic waistband 68 can cover a distance 74, measured parallel to the longitudinal centerline X—X of the absorbent article 10, of between about 0.5 inches (1.27 cm) to about 6 inches (15.24 cm). The distance 74 can be the same in the first zone 20 of the front portion 12 and the back portion 14. Preferably, the distance 74 ranges from between about 0.5 inches (1.27 cm) to about 6 inches (15.24 cm). The elastic waistband 68 may optionally extend into the second zone 22 of the front portion 12 and/or the back portion 14. The elastic waistband 68 can cover a distance 76, measured parallel to the longitudinal centerline X—X, of between about 0.5 inches (1.27 cm) to about 10 inches (25.4 cm) in the second zone 22 in the front and back portions, 12 and 14 respectively. The elastic waistband 68 may cover a greater distance 72 in the back portion 14 than in the front portion 12. Additionally, the elastic waistband 68 may cover a greater distance 74 in the back portion 14 than in the front portion 12 of the absorbent article 10.

Referring to FIGS. 1 and 3, leg elastic 78 can be positioned circumferentially around each of the leg openings 54. The leg elastic 78 may be disposed between the outer cover 32 and the bodyside liner 36. As shown in FIGS. 1 and 3, the leg elastic 78 may comprise 3 elastic strands. Furthermore, the leg elastic 78 may extend completely around the entire circumference of each leg opening 54, as shown in FIG. 1. Alternatively, the leg elastic 78 may be comprised of two or more individual sections positioned circumferentially around the leg openings 54. Referring to FIG. 3, the leg elastic 78 is shown as having a pair of front leg elastics 80, a pair of back leg elastics 82, and a pair of crotch elastics 84 positioned circumferentially around the leg opening 54.

The leg elastic 78 is depicted in FIGS. 1 and 3 as being three separate strands of elastic material. It should be noted that from 1 to about 12 elastic strands could be utilized if desired. It has been found that three elastic strands provide adequate elastic strength to form gathers around each leg opening 54. The leg elastic 78 can be secured at intermittent sites to the outer cover 32 and/or to the bodyside liner 36 by an adhesive, by ultrasonic bonding, by heat and/or pressure bonds or by some other means known to those skilled in the art. The leg elastic 78 can be in the form of long or short elastic strands, elastic tapes, ribbons, yarns, etc. The leg elastic 78 can have a cross-sectional configuration that is flat, square, rectangular, circular, oval or some other shape. A good material from which the leg elastic 78 can be formed is LYCRA®. LYCRA® is a registered trademark of E. I. DuPont Nemours & Company, a business that has offices at 1002 Market Street, Wilmington, Del. 19801.

Referring to FIG. 3, each of the front leg elastics 80 are positioned adjacent to a pair of front leg edges 86. Each of the pair of front leg edges 86 is substantially linear in configuration and each extends laterally inward from one of the first front side edge 56 or the second front side edge 60 toward the crotch portion 16. Preferably, at least about 70 percent of the length of each of the front leg edges 86 are linear in configuration. Each of the pair of front leg edges 86 are aligned at an angle alpha ($\alpha$) to the longitudinal centerline X—X of the absorbent article 10. The angle alpha ($\alpha$) can range from about 62 degrees to about 99 degrees. Preferably, the angle alpha ($\alpha$) can range from between 74 degrees to 91 degrees, and most preferably, the angle alpha ($\alpha$) is at least about 85 degrees. The angling of the pair of front leg edges 86 relative to the longitudinal centerline X—X ensures a better contouring of the absorbent article 10 to the body and provides a comfortable fit with reduced bunching. The linear configuration of the front leg edges 86 can also allow for increased manufacturing speeds.

The pair of front leg elastics 80 are located along and are preferably aligned parallel to the front leg edges 86. Each of the front leg elastics 80 has a first end 88 located adjacent to or conterminous with the first or second front side edge 56 or 60 respectively. Preferably, each of the first ends 88 are spaced slightly inward of the first and second front side edges 56 and 60. The pair of front leg elastics 80 terminates at a second end 90. Each second end 90 is located away from the outer periphery of the absorbent core 18. The exact distance the second ends 90 are spaced from the outer periphery of the absorbent core 18 can vary from between about 1 millimeter to about 100 millimeters, and preferably, the distance is less than about 50 millimeters.

Still referring to FIG. 3, the absorbent article 10 also includes a pair of back leg elastics 82. The pair of back leg elastics 82 may be secured between the outer cover 32 and/or the bodyside liner 36. Each of the pair of back leg elastics 82 is positioned adjacent to one of the pair of back leg edges 92. Each of the pair of back leg edges 92 is substantially linear in configuration and extends inward toward the crotch portion 16 from the first and second back side edges, 58 and 62 respectively. Preferably, at least about 70 percent of the length of each of the pair of back leg edges 92 are linear in configuration. Each of the pair of back leg edges 92 is aligned at an angle beta ($\beta$) to the longitudinal centerline X—X of the absorbent article 10. The angle beta ($\beta$) can range from between about 45 degrees to about 89 degrees. Preferably, the angle ($\beta$) can range from between about 55 degrees to 87 degrees, and most preferably, the angle beta ($\beta$) is from between about 61 degrees to about 76 degrees. The angling of the back leg edges 92 relative to the longitudinal centerline X—X ensures a better contouring of the absorbent article 10 to the body and provides a comfortable fit with reduced bunching. The linear configuration of the back leg edges 92 can also allow for increased manufacturing speeds.

Each of the pair of back leg elastics 82 are located along and are preferable aligned parallel to the pair of back leg edges 92. Each of the back leg elastics 82 has a first end 94 located adjacent to or conterminous to one of the first and second back side edges, 58 and 62. Preferably, each of the first ends 94 is spaced slightly inward from the first and second back side edges, 58 and 62. The back leg elastics 82 should extend toward the absorbent core 18 but should stop short thereof. Each of the pair of back leg elastics 82 terminates at a second end 96. Each second end 96 is located away from the outer periphery of the absorbent core 18. The exact distance can vary from between about 1 millimeter to about 100 millimeters, and preferably, the distances is less than about 50 millimeters.

The absorbent article further includes a pair of crotch elastics 84. Each of the pair of crotch elastics 84 is positioned adjacent to an edge 98 of the pair of leg openings 54, located intermediate the front and back leg elastics, 80 and 82 respectively. Each of the pair of crotch elastics 84 is positioned slightly inward from and generally follows the shape of the edges 98. The exact distance that the crotch elastics 84 are positioned and secured inward of the edges 98 should range from between about 2.5 millimeter to about 20.3 millimeters. Preferably, the distance that each of the pair of crotch elastics 84 are secured inward of the edges 98 will be from about 3.8 millimeters to about 12.7 millimeters, and most preferably, will be secured inward about 6.7 millimeters from the edges 98.

As noted above, each of the pair of crotch elastics 84 is positioned adjacent to and preferably is aligned parallel to the edges 98 of the crotch portion 16. Each of the pair of crotch elastics 84 has a first end 100 and a second end 102. Each of the crotch elastics 84 is positioned intermediate one of the front and back leg elastics, 80 and 82 respectively. Each of the first ends 100 of each crotch elastic 84 is separated from the second end 90 of one of the front leg elastics 80 by a first gap 104. The dimension of each of the first gaps 104 is denoted by "$D_1$" and $D_1$ can be at least about 3.2 millimeters in length. More preferably, the dimension $D_1$ of each of the first gaps 104 ranges from between about 12.7 mm to about 51 mm. The $D_1$ dimension is measured when the absorbent article 10 is in a flat extended orientation similar to that depicted in FIG. 3.

Likewise the second end 102 of each of the pair of crotch elastics 84 is separated from the second end 96 of the pair of back leg elastics 82 by a second gap 106. The dimension of each of the second gaps 106 is denoted as "$D_2$" and $D_2$ can be at least about 3.2 millimeters in length. Preferably, the dimension $D_2$ of each of the second gaps 106 ranges from between about 6.4 mm to about 229 mm. More preferably, the dimension $D_2$ of each of the second gaps 106 ranges from between about 9.5 mm to about 127 mm. Most preferably, the dimension $D_2$ of each of the second gaps 106 ranges from between about 12.7 mm to about 51 mm. The $D_2$ dimension is measured when the absorbent article is in a flat extended orientation similar to that depicted in FIG. 3.

Referring back to FIG. 2, gathers 108 are formed around the leg openings 54 as the leg elastic 78 contracts. The gathers 108 will form a snug fit around the entire circumference of each of the leg openings 54. A snug fit is around the wearer's thighs is important to prevent the leakage of body fluid around the leg openings 54.

In one embodiment, as shown in FIG. 3, the first and second pairs of gaps, 104 and 106 respectively, cooperate with the front, back and crotch elastics 80, 82 and 84 to form the gathers 108 (not shown). The two pairs of gaps 104 and 106 will prevent the adjacent front, back and crotch pairs of elastics 80, 82 and 84 from overlapping one another and forming bumps and/or humps around the leg openings 54. By eliminating such bumps and humps one can prevent the leakage of body fluid through the leg openings 54. It is very important that fluid leakage from around the leg openings 54 be eliminated because if such leakage occurs, the usefulness of the absorbent article 10 is compromised.

Even though two pairs of gaps 104 and 106 are present in the stretched out, flat orientation shown in FIG. 3, the contraction force of the front, back and crotch pairs of leg elastics 80, 82 and 84 will cause the gathers 108 to form. The force of the front, back and crotch pairs of leg elastic 80, 82 and 84 positioned adjacent to the gaps 104 and 106 will cause the material forming the outer cover 32 and the bodyside liner 36 to fit snug against the thighs of the wearer during use. No fluid channels will occur at the locations of the first and second pairs of gaps 104 and 106. This will assure that no body fluid will be able to leak out through these locations during normal use.

Referring to FIG. 3, the absorbent core 18 positioned in the crotch portion 16 of the absorbent article 10 may extend into the second zone 22 of the front portion 12 and the back portion 14. Preferably, a front edge 110 and a back edge 112 of the absorbent core 18 are positioned between the two demarcation lines 24. Alternatively, the front edge 110 and the back edge 112 of the absorbent core 18 can abut the pair of demarcation lines 24. Furthermore, the back edge 112 of the absorbent core 18 can overlay at least a portion of the elastic waistband 68 in the second zone 22 of the back portion 14.

Returning again to FIG. 1, the crotch portion 16 has a width $W_3$ and the width $W_2$ of the absorbent core 18 may be less than the width $W_3$ such that the opposite side edges 114 of the absorbent core 18 are positioned laterally inboard of the leg elastic 78 in the crotch portion 16. Alternatively, as shown in FIG. 3, the width $W_2$ of the absorbent core 18 may be substantially equal to the width $W_3$ of the crotch portion 16 such that the opposite side edges 114 of the absorbent core 18 are conterminous with the edges 98 of the crotch portion 16. Preferably, the absorbent core 18 is positioned in the crotch section 16 such that the opposite side edges 116 of the absorbent layer 44 are laterally positioned inboard of the crotch elastics 84. The absorbent core 18 can be attached to the outer cover 32 and/or the bodyside liner 36 by an adhesive, heat and/or pressure bond, or other means known to one skilled in the art.

In an alternative embodiment (not shown), the crotch elastics 84 may be secured between the liquid impermeable baffle 42 and the liquid permeable cover 40 of the absorbent core 18. Each of the pair of crotch elastics 84 is positioned adjacent to and, preferably, aligned parallel to the side edges 114 of the absorbent core 18. Each of the pair of crotch elastics 84 is positioned slightly inward from the side edges 114. Additionally, each of the pair of crotch elastics 84 is positioned slightly outboard of the side edges 116 of the absorbent layer 44. Positioning the crotch elastics 84 outboard of the absorbent layer 44 is important to avoid bunching the absorbent layer 44 thereby compromising the fit and function of the absorbent article 10.

The absorbent core 18 may be attached to the outer cover 32 and/or the bodyside liner 36 by an adhesive, heat and/or pressure bond, or other means known to one skilled in the art. The absorbent core 18 is attached such that the contractive force of the crotch elastics 84 will cause gathers 108 to form and will cause the material forming the outer cover 32 and/or the bodyside liner 36 to fit snug against the thighs of the wearer during use The absorbent core 18 is positioned in the crotch portion 16 such that each of the crotch elastics 84 is positioned intermediate of one of the front and back leg elastics, 80 and 82 respectively. Further, the absorbent core 18 is positioned in the crotch portions 16 such that each of the first ends 100 of each crotch elastic 84 is separated from the second end 90 of one of the front leg elastics 80 by a first gap 104. The dimension of each of the first gaps 104 is denoted by "$D_1$" and $D_1$ can be at least about 3.2 millimeters in length. More preferably, the dimension $D_1$ of each of the first gaps 104 is from between about 12.7 mm to about 51 mm.

Likewise, the absorbent core 18 is positioned in the crotch portion 16 such that the second end 102 of each of the pair of crotch elastics 84 is separated from the second end 96 of the pair of back leg elastics 82 by a second gap 106. The dimension of each of the second gaps 106 is denoted as "$D_2$" and $D_2$ can be at least about 3.2 millimeters in length. Preferably, the dimension $D_2$ of each of the second gaps 106 ranges from between about 6.4 mm to about 229 mm. More preferably, the dimension $D_2$ of each of the second gaps 106 ranges from between about 9.5 mm to about 127 mm. Most preferably, the dimension $D_2$ of each of the second gaps 106 ranges from between about 12.7 mm to about 51 mm.

Figure 4:
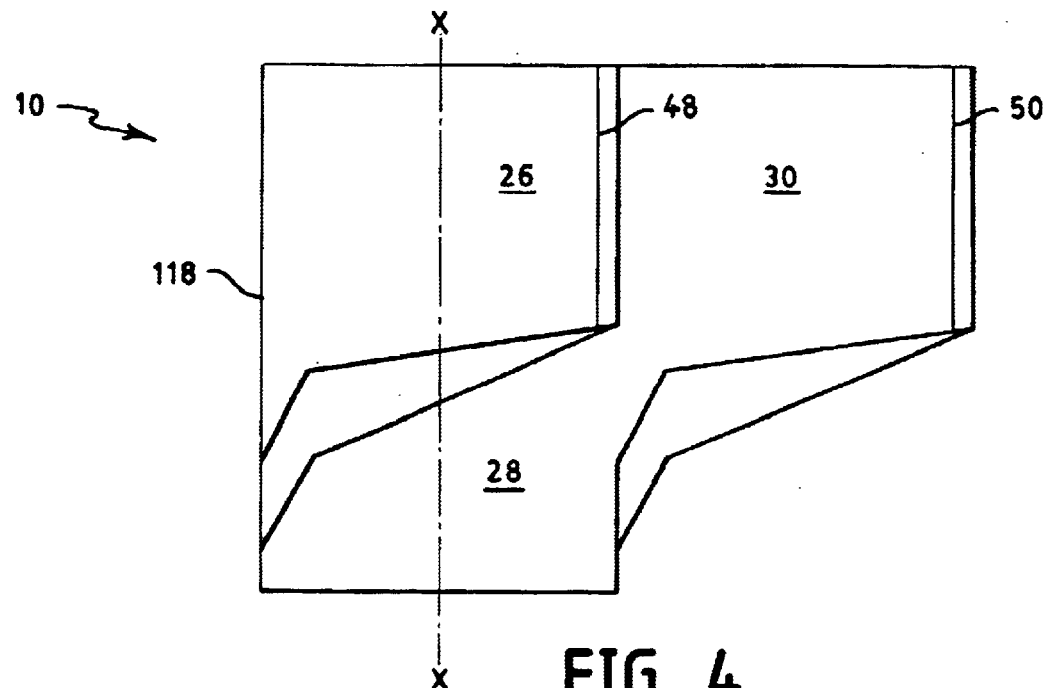
FIG. 4 is a planar view of the absorbent article when the first section of the front and back portions is longitudinally folded over the second section.
Figure 5:
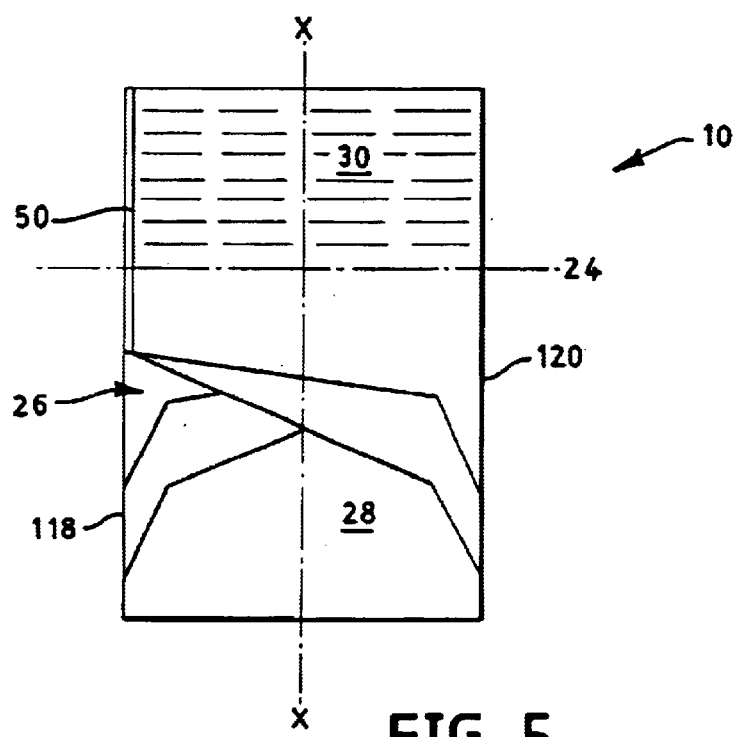
FIG. 5 is a planar view of the absorbent article when the third section of the front and back portions is longitudinally folded over the first section.
Figure 6:
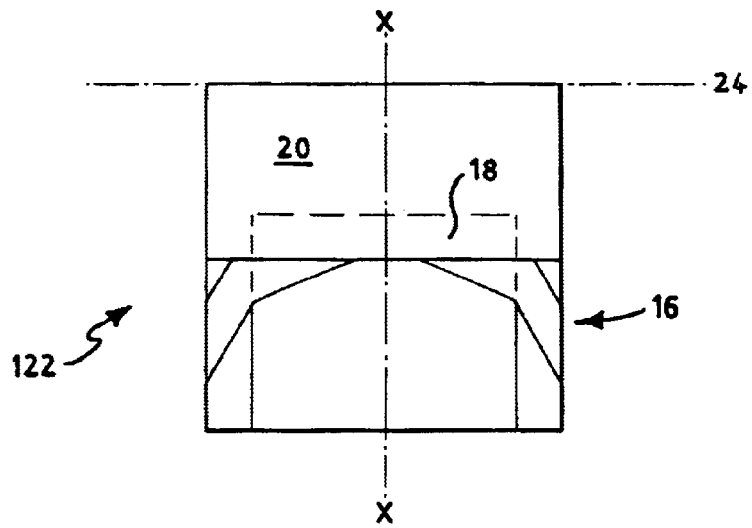
FIG. 6 is a planar view of the folded absorbent article when the first zone of the front and back portions of the absorbent article is transversely folded at the demarcation line over at least a portion of the crotch portion.

Referring to FIGS. 4 through 6, a way of folding an absorbent article 10 is depicted, starting with FIG. 4, when the first section 26 of the front portion 12 and the back portion 14 is longitudinally folded over the second section 28 to form a first longitudinal fold line 118. The first side seam 48 is positioned laterally outboard of the longitudinal centerline X—X of the absorbent article 10 and may overlap a portion of the third section 30. With reference to FIG. 5, the absorbent article 10 is shown when the third section 30 of the front portion 12 and the back portion 14 is longitudinally folded over the first section 26 to form a second longitudinal fold line 120. The second side seam 50 is positioned laterally outboard of the longitudinal centerline X—X of the absorbent article 10. When the absorbent article 10 is folded along the second longitudinal fold line 120, the first and second side seams, 48 and 50 respectively, are aligned approximately parallel to one another. Furthermore, when the third section 30 is folded along the second longitudinal fold line 120 such that the third section 30 overlaps the first section 26, no gap or space is present between the first and second side seams, 48 and 50 respectively. This folded configuration is important to reduce the overall width of the absorbent article 10 and provide a more compact product that can be placed in a smaller, more economical package. Preferably, when the absorbent article 10 has been folded as depicted in FIG. 5, the absorbent article 10 should have a width that is approximately one third or less of its width in an open position. FIG. 6 illustrates a folded absorbent article 122. The first zone 20 of the front portion 12 and the back portion 14 is transversely folded along the demarcation line 24 over at least a portion of the crotch portion 16 to form the folded absorbent article 122. When the absorbent article 10 is folded in this manner, the absorbent core 18 will contain only one transverse fold line located approximately along transverse centerline Y—Y thereby minimizing the chance of fluid leakage.

Figure 7:
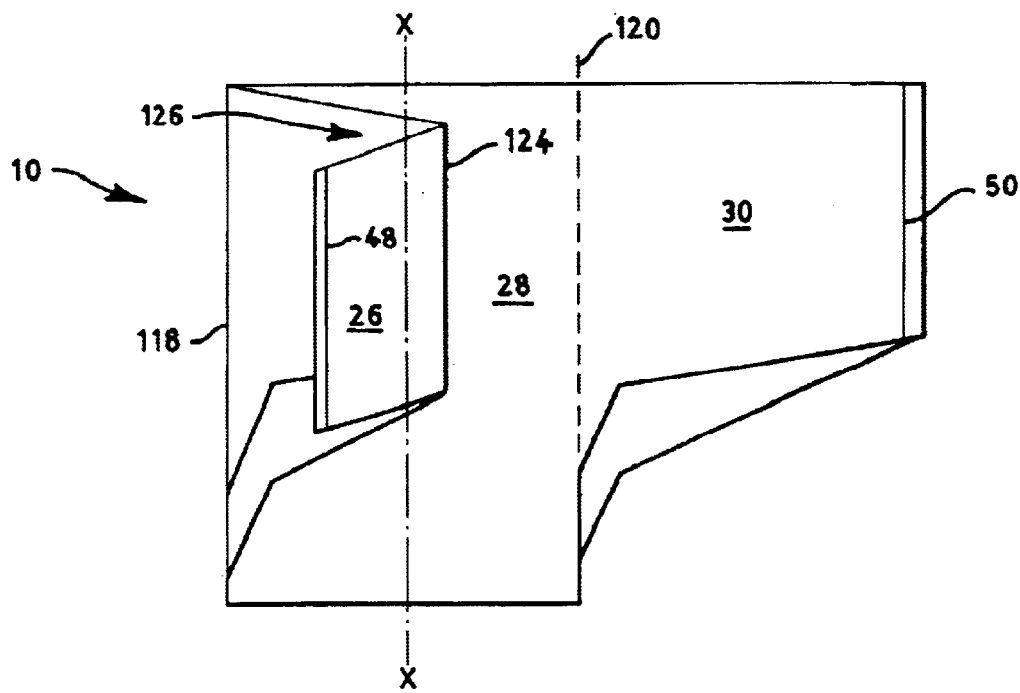
FIG. 7 is a planar view of an alternative embodiment showing the first section longitudinally folded along a third longitudinal fold line to form a longitudinal pleat in the first section of the front and back portions of the absorbent article.

Referring now to FIG. 7, an alternative folding embodiment is depicted wherein the first section 26 of the front portion 12 and the back portion 14 of the absorbent article 10 is longitudinally folded over the second section 28 to form a first longitudinal fold line 118. The first section 26 is longitudinally folded to form a third longitudinal fold line 124 such that the first side seam 48 is positioned adjacent to the first longitudinal fold line 118 to form a longitudinal pleat 126 in the first section 26. The third section 30 of the front portion 12 and the back portion 14 is longitudinally folded over the first section 26 to form a second longitudinal fold line 120. The second side seam 50 is positioned laterally outboard of longitudinal centerline X—X of absorbent article 10. The second side seam 50 may optionally be positioned adjacent to the first longitudinal fold line 118 or the second side seam 50 may extend beyond the first longitudinal fold line 118 (not shown).

As shown in FIGS. 1 and 3, the side edges 116 of the absorbent layer 44 are positioned laterally inboard of the first longitudinal fold line 118 and the second longitudinal fold line 120. The absorbent article 10 may be longitudinally folded such that the first and second longitudinal fold lines, 118 and 120 respectively, are conterminous with the edges 98 of the crotch portion 16. Preferably, the absorbent article 10 may be longitudinally folded such that the first and second longitudinal fold lines 118 and 120 are formed intermediate of the crotch elastics 84 and the side edge 116 of the absorbent layer 44. More preferably, the absorbent article 10 is longitudinally folded such that the first and second longitudinal fold lines, 118 and 120 respectively, abut the side edges 116 of the absorbent layer 44. The first and second longitudinal fold lines 118 and 120 are formed laterally outboard of the side edges 116 of the absorbent layer 44 to prevent adding additional bulk to the folded absorbent article 122. Furthermore, the first and second fold lines 118 and 120 are preferably formed abutting the side edges 116 of the absorbent layer 44 to effectively contain the unelasticized portion 128 of the front portion 12 and the back portion 14 within the folded absorbent article 122. It is important to contain the unelasticized portion 128 of the front and back portions 12 and 14 to reduce the bulk of the folded absorbent article 122 provide a neater folded absorbent article 122 that is easier to handle during the packaging process.

While the invention has been described in conjunction with several specific embodiments, it is to be understood that many alternative, modifications and variations will be apparent to those of skill in the art in light of the foregoing description. Accordingly, this invention is intended to embrace all such alternatives, modifications and variations that fall within the spirit and scope of the appended claims.

We claim:

1. A folded absorbent article comprising:
    a) a front portion and a back portion joined together by a crotch portion, said front portion is joined to said back portion by first and second side seams to form an absorbent article having a waist opening and a pair of leg openings, each of said front and back portions having a first zone and a second zone with a demarcation line therebetween, said absorbent article having a longitudinal centerline and a transverse centerline, each of said front and back portions having a first section, a second section and a third section;
    b) an absorbent core positioned in said crotch portion; and
    c) elastic positioned in at least said first zone of at least one of said front and back portions to define an elastic waistband, said first section is longitudinally folded over said second section such that said first side seam is positioned laterally outboard of said longitudinal centerline to form a first longitudinal fold line, said third section is longitudinally folded over said first section such that said second side seam is positioned laterally outboard of said longitudinal centerline to form a second longitudinal fold line, and said first zone is transversely folded along said demarcation line over at least a portion of said crotch portion to form a folded absorbent article.

2. The folded absorbent article of claim 1 wherein said elastic is positioned transversely across at least a portion of said first zone to form said elastic waistband in said front and back portions.

3. The folded absorbent article of claim 2 wherein said elastic waistband includes multiple elastic strands.

4. The folded absorbent article of claim 3 wherein at least one of said multiple elastic strands is positioned at least about 0.25 inches above said demarcation line in said first zone.

5. The folded absorbent article of claim 3 wherein at least one of said multiple elastic strands abuts said demarcation in said front portion.

6. The folded absorbent article of claim 1 wherein said elastic waistband has a distance measured parallel to said longitudinal centerline of from between about 0.5 inches to about 6 inches in said first zone.

7. The folded absorbent article of claim 6 wherein said elastic waistband has a distance measured parallel to said longitudinal centerline of from between about 0.5 inches to about 10 inches in said second zone.

8. The folded absorbent article of claim 1 wherein said elastic waistband has a greater distance measured parallel to said longitudinal centerline in said back portion than in said front portion.

9. The folded absorbent article of claim 1 wherein said absorbent core extends into said second zone of said front and back portions.

10. A folded absorbent article comprising:
   a) a front portion and a back portion joined together by a crotch portion, said front portion is joined to said back portion by first and second side seams to form an absorbent article having a waist opening and a pair of leg openings, each of said front and back portions having a first zone and a second zone with a demarcation line therebetween, said absorbent article having a longitudinal centerline and a transverse centerline, each of said front and back portions having a first section, a second section and a third section;
   b) an absorbent core positioned in said crotch portion, said absorbent core having a front edge and a back edge;
   c) a pair of leg elastics surrounding said pair of leg openings; and
   d) multiple elastic strands positioned transversely across said front and back portions to define an elastic waistband, said elastic waistband having a width measure parallel to said longitudinal centerline from between about 0.5 inches to about 10 inches, said first section is longitudinally folded over said second section such that said first side seam is positioned laterally outboard of said longitudinal centerline to form a first longitudinal fold line, said third section is longitudinally folded over said first section such that said second side seam is positioned laterally outboard of said longitudinal centerline to form a second longitudinal fold line, and said first zone is transversely folded along said demarcation line over at least a portion of said crotch portion to form a folded absorbent article.

11. The folded absorbent article of claim 10 wherein said multiple elastic strands are uniformly spaced apart from each other.

12. The folded absorbent article of claim 10 wherein said multiple elastic strands are non-uniformly spaced apart from each other.

13. The absorbent article of claim 10 wherein said absorbent core extends into said second zone of said front and back portions.

14. The folded absorbent article of claim 10 wherein said first section is longitudinally folded to form a third longitudinal fold line such that said first side seam is positioned adjacent to said first longitudinal fold line to form a longitudinal pleat in said first section.

15. The folded absorbent article of claim 10 wherein said front edge of said absorbent core abuts said demarcation line in said front portion.

16. A folded absorbent article comprising:
   a) a front portion and a back portion joined together by a crotch portion, said front portion is joined to said back portion by first and second side seams to form an absorbent article having a waist opening and a pair of leg openings, each of said front and back portions having a first zone and a second zone with a demarcation line therebetween, said absorbent article having a longitudinal centerline and a transverse centerline, each of said front and back portions having a first section, a second section and a third section;
   b) an absorbent core positioned in said crotch portion; and
   c) multiple elastic strands positioned in said first zone of said front and back portions to define an elastic waistband, said first section is longitudinally folded over said second section such that said first side seam is positioned laterally outboard of said longitudinal centerline to form a first longitudinal fold line, said first section is longitudinally folded to form a third longitudinal fold line such that said first seam is positioned adjacent to said first longitudinal fold line to form a longitudinal pleat in said first section, said third section is longitudinally folded over said first section such that said second side seam is positioned laterally outboard of said longitudinal centerline to form a second longitudinal fold line, and said first zone is transversely folded along said demarcation line over at least a portion of said crotch portion to form a folded absorbent article.

17. The folded absorbent article of claim 16 wherein said multiple elastic strands are positioned transversely across at least a portion of said front and back portions to form said waistband.

18. The folded absorbent article of claim 17 wherein said elastic waistband has a distance measured parallel to said longitudinal centerline of between about 0.5 inches to about 6 inches.

19. The folded absorbent article of claim 16 wherein said elastic waistband has a greater distance measured parallel to said longitudinal centerline in said back portion than in said front portion.

20. The folded absorbent article of claim 16 wherein said absorbent core extends into said second zone of said front and back portions.

* * * * *